(12) United States Patent
Deinzer et al.

(10) Patent No.: US 8,194,957 B2
(45) Date of Patent: Jun. 5, 2012

(54) REGISTRATION METHOD WITH THREE-DIMENSIONAL REPRESENTATION OF A VASCULAR TREE AS A FUNCTION OF BLOOD FLOW

(75) Inventors: Frank Deinzer, Röthenbach (DE); Esther-Sabrina Platzer, Jena (DE)

(73) Assignee: Siemens Aktiengesellschaft, München (DE)

( * ) Notice: Subject to any disclaimer, the term of this patent is extended or adjusted under 35 U.S.C. 154(b) by 932 days.

(21) Appl. No.: 12/283,883

(22) Filed: Sep. 16, 2008

(65) Prior Publication Data

US 2009/0074277 A1 Mar. 19, 2009

(30) Foreign Application Priority Data

Sep. 18, 2007 (DE) .......................... 10 2007 044 406

(51) Int. Cl.
*G06K 9/00* (2006.01)
(52) U.S. Cl. .................. 382/130; 382/294; 600/431
(58) Field of Classification Search .................. None
See application file for complete search history.

(56) References Cited

U.S. PATENT DOCUMENTS

2006/0293579 A1* 12/2006 Schmitt et al. ............... 600/407

OTHER PUBLICATIONS

H. Schmitt, M. Grass, V. Rasche, O. Schramm, S. Haehnel, and K. Sartor, "An X-Ray-Based Method for the Determination of the Contrast Agent Propagation in 3-D Vessel Structures", Mar. 2002, IEEE Transactions on Medical Imaging, vol. 21, No. 3, pp. 251-262.*

Carlos O.S. Sorzano, Philippe Thevenaz, and Michael Unser, "Elastic Registration of Biological Images Using Vector-Spline Regularization", Apr. 2005, IEEE Transactions on Biomedical Engineering, vol. 52, No. 4, pp. 652-663.*
William R. Brody, "Digital Subtraction Angiography", Jun. 1982, IEEE Transactions on Nuclear Science, vol. NS-29, No. 3, pp. 1176-1180.*
Esther-Sabrina Platzer; "Visualisierung von Blutfluss im 3-D aus 2-D-Angiogrammen"; Platzer; Diplomarbeit, Universität Koblenz-Landau und Siemens Medical Solutions Forchheim, Aug. 2006 http://www.uni-koblenz.de/FB4/Publications/Theses/ShowThesis?id=1893#refl vorr. nicht veröffentlicht; Others; 2006.
H. Schmitt et al.; "Reconstruction of blood propagation in three-dimensional rotational X-ray angiography (3D-RA)"; Schmitt et al.; Computerized Medical Imaging and Graphics, Oct. 2005; vol. 29(7), pp. 507-520, Epub Sep. 2, 2005; Magazine; 2005.
Tobias Hüllmandel; "Räumliche und zeitliche Rekonstruktionen in der Neuroradiologie Huellmandel"; Diplomarbeit an dem Lehrstuhl für Informatik II der Bayerischen Julius-Maximilians-Universität Würzburg; Others; 2004.
Guy Shechter, Frédéric Devemay, Eve Coste-Manière, Arshed Quyyumi, and Elliot R. McVeigh; Three-Dimensional Motion Tracking of Coronary Arteries in Biplane Cineangiograms Shechter et al.; IEEE Transactions on Medical Imaging, vol. 22, No. 4, Apr. 2003, pp. 493-503; Magazine; 2003.

* cited by examiner

*Primary Examiner* — Claire X Wang
*Assistant Examiner* — Siamak Harandi

(57) ABSTRACT

A three-dimensional volume data record contains a vascular tree. A two-dimensional projection image is an image of an actual fill state, to which the vascular tree is filled with a contrast agent at an acquisition time. The volume data record and the projection image are registered in relation to one another by means of the set of imaging parameters. A computation facility determines an expected target fill state, which describes which parts of the vascular tree should be filled with contrast agent at acquisition time in the three-dimensional volume data record. The computation facility determines the set of imaging parameters based on the target fill state and the projection image.

15 Claims, 7 Drawing Sheets

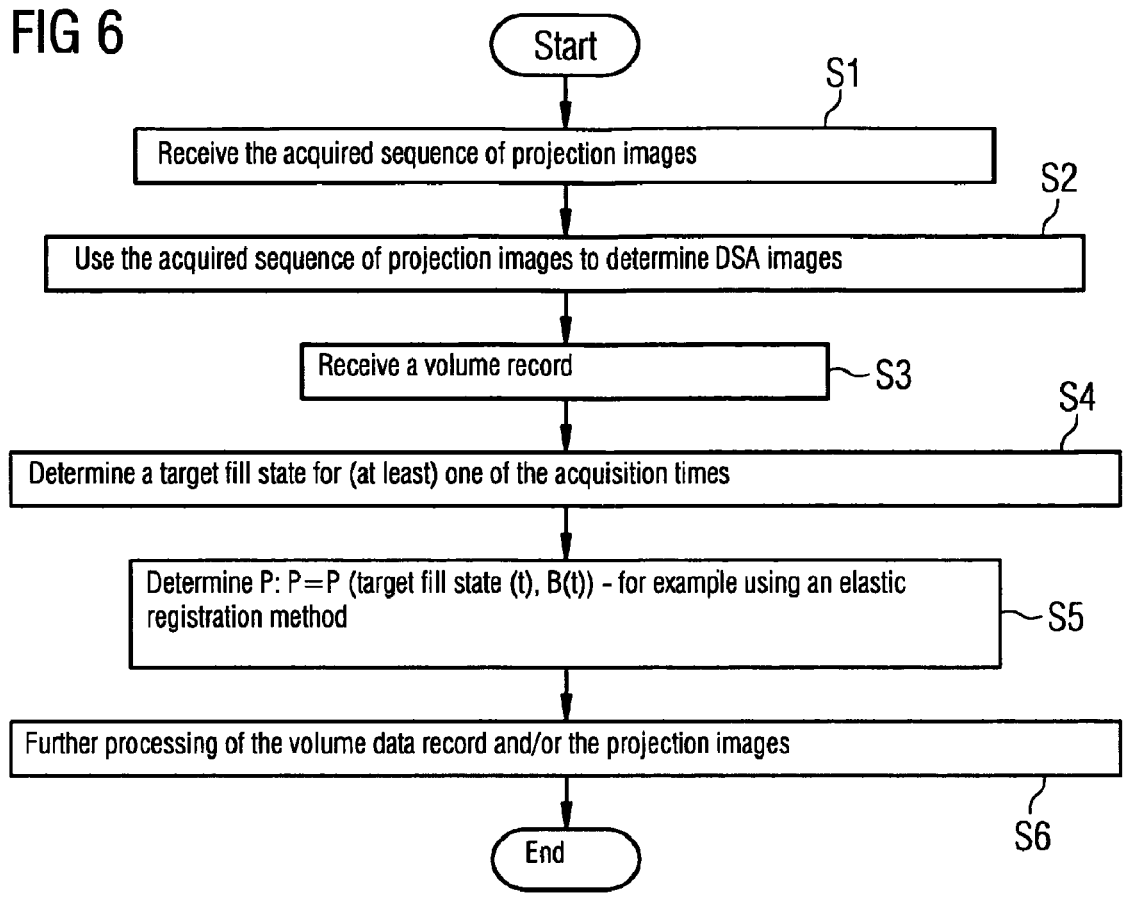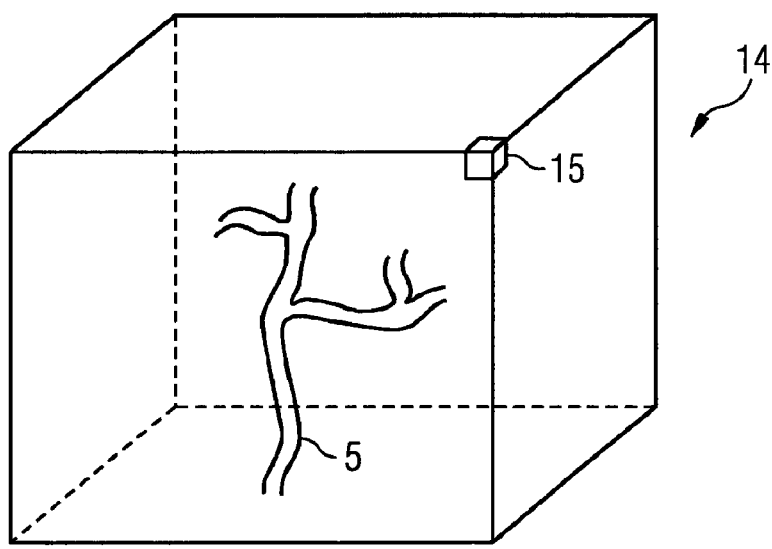

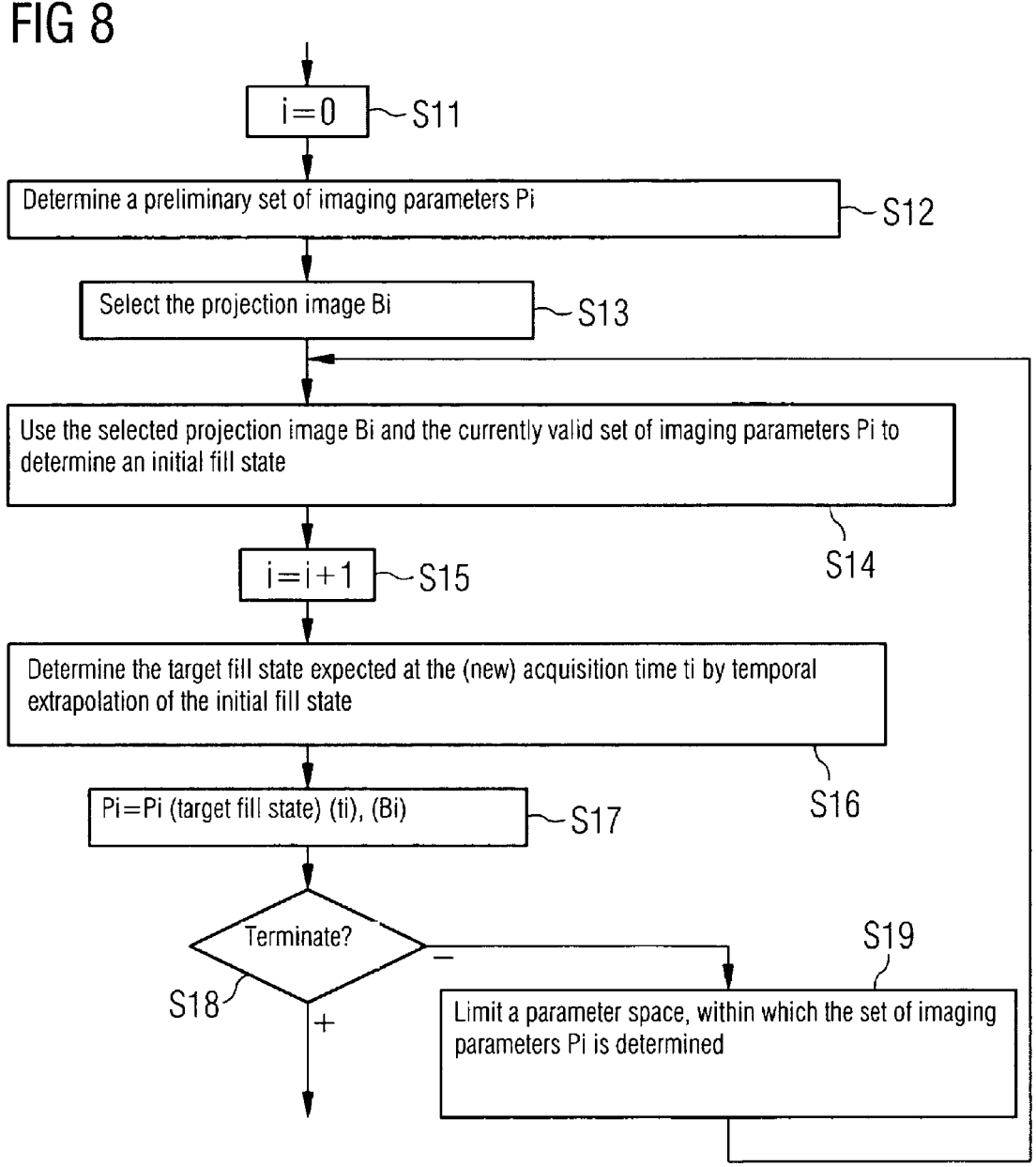

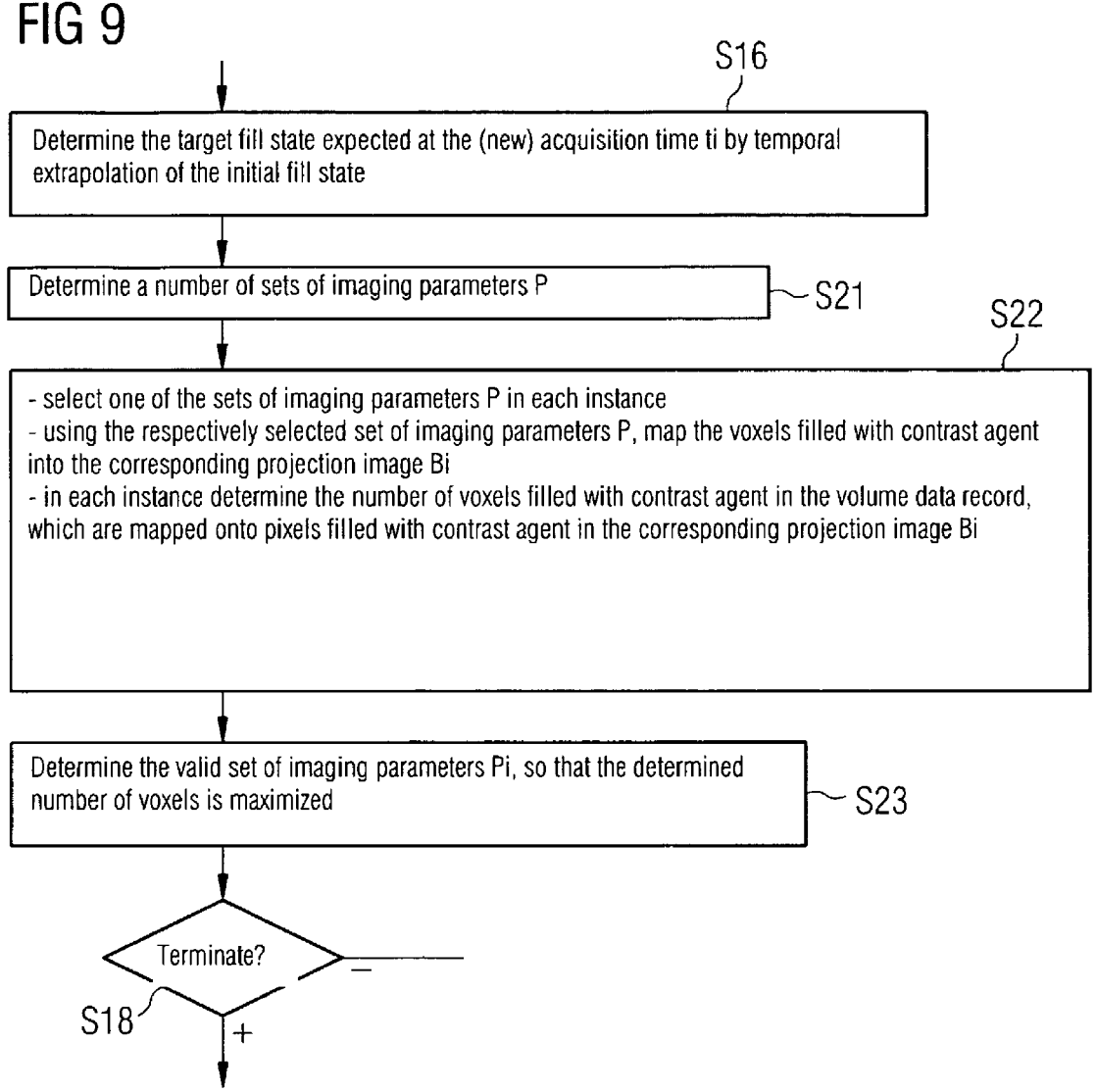

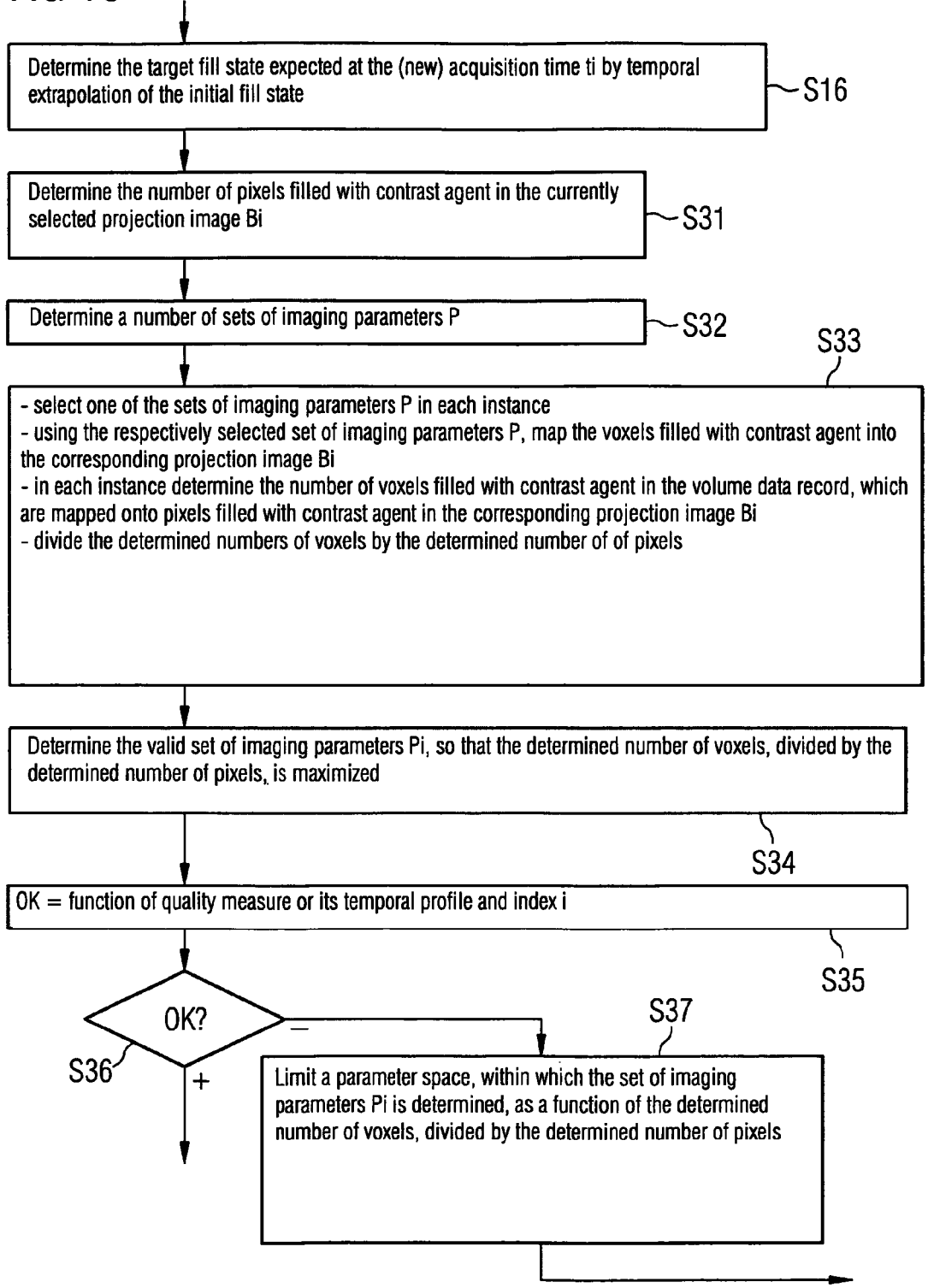

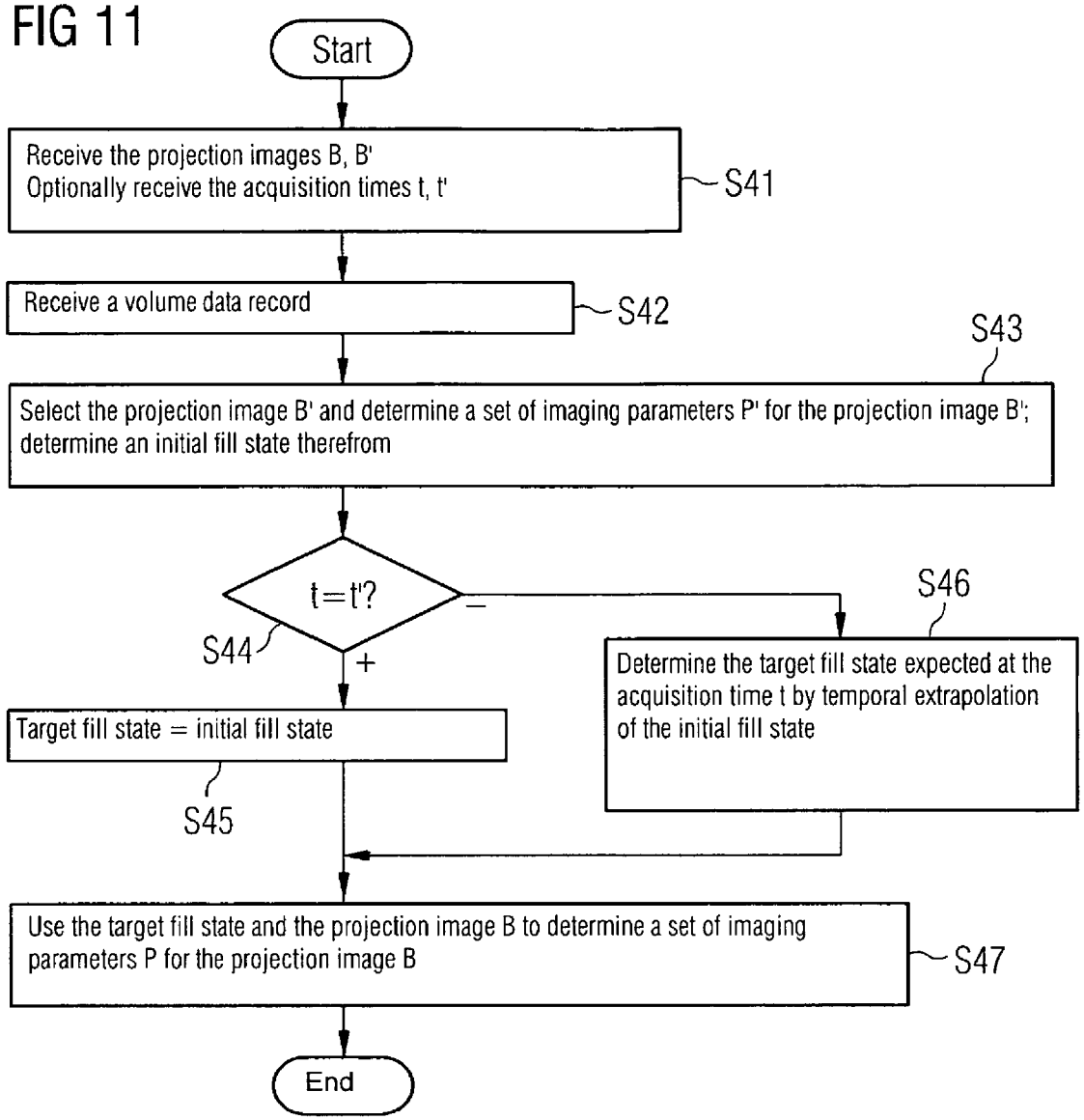

REGISTRATION METHOD WITH THREE-DIMENSIONAL REPRESENTATION OF A VASCULAR TREE AS A FUNCTION OF BLOOD FLOW

CROSS REFERENCE TO RELATED APPLICATIONS

This application claims priority of German application No. 10 2007 044 406.2 filed Sep. 18, 2007, which is incorporated by reference herein in its entirety.

FIELD OF THE INVENTION

The present invention relates to a registration method with three-dimensional representation of a vascular tree as a function of blood flow.

BACKGROUND OF THE INVENTION

The imaging methods generally used for vascular diagnosis include both two-dimensional digital subtraction angiography (DSA) and three-dimensional rotational angiography. Both modalities have specific advantages in respect of diagnostic options. However both modalities also have specific disadvantages. They cannot simply be interchanged with one another.

Certain diagnosis processes require both temporal and structural information about blood flow. In such instances both technologies have to be deployed. However in order for the treating physician to be able to investigate certain facts in both data records under virtually identical conditions and particularly from the same viewpoint, the two-dimensional angiography images and the three-dimensional volume data record have to be registered in relation to one another.

Registration is often problematic, since a vascular tree that is permanently filled in its entirety with contrast agent is used for the reconstruction of the three-dimensional volume data record. The object of two-dimensional subtraction angiography in contrast is precisely the opposite, being to acquire the temporal propagation of a contrast agent in the vascular tree. Therefore the two-dimensional DSA sequence often contains no projection, which contains a vascular tree that is entirely (or at least essentially entirely) filled with contrast agent. This significantly impedes registration, as non-identical states have to be linked to one another. Add to this that in some instances during the recording of a 2D angiography image the patient moves and/or the vessels in the body are in constant (even if only slight) motion due to the pulse and blood pressure. Methods for compensating for such motion are known but compensation is difficult and only possible to a limited degree.

Registration methods per se are known from the prior art. Reference is made purely by way of example to the specialist article "Reconstruction of blood propagation in three-dimensional rotational X-ray angiography (3D-RA)" by H. Schmitt et al., which appeared in Computerized Medical Imaging and Graphics, vol. 29, pages 507 to 520, 2005.

To carry out registration it is known in the prior art that one of the two-dimensional images of an angiography sequence can be selected for example. In this process the angiography image showing the maximum degree of filling is preferably selected. Selection can be either automatic or manual. In this instance the selected DSA image is registered in relation to the volume data record. Because the recording geometry is generally kept constant during acquisition of the entire DSA sequence, registration is therefore valid for all the other images in the DSA sequence.

In other instances a "summation image" is determined based on all the projection images in the DSA sequence. For example the temporal gradient of the intensity of the individual images can be determined by pixel by pixel and each pixel, for which the temporal change deviates significantly from zero at least once, can be marked as being associated with the vascular tree. With this embodiment all the marked pixels correspond to the summation image, which is registered in relation to the volume data record.

Other methods are also known and possible. A method is thus described by way of example in the above-mentioned specialist article by H. Schmitt et al., wherein the entropy over time is determined for each pixel. The entropy codes the measure of random information in a system. It is defined as $$H(x) = -\sum_{z \in Z} p(X = z) \log_2 p(X = z)$$

p(X=z) here defines the probability that the pixel X will assume the color or gray-scale value z. Z is all the possible color or gray-scale values. In the context of the application this means that the intensity values of pixels associated with the vascular tree change markedly when considered over the entire sequence. The intensity change takes place precisely when the relevant part of the vascular tree has contrast agent flowing through it. The information content of the relevant pixel is defined by $\log_2 p(X=z)$. Either a very high or a very low value is assigned to the respective pixel depending on the entropy determined. It is possible in this manner to separate the vascular tree clearly from the background.

To determine the set of imaging parameters in the prior art according to the specialist article by H. Schmitt et al. the three-dimensional volume data record is not used directly. Instead an artificial projection of the volume data record is generated. Registration takes place between the two-dimensional summation image on the one hand and the artificial, likewise two-dimensional, projection of the volume data record on the other hand. However this procedure involves a significant computation outlay, as the artificial projection has to be determined as well as the determination of the summation image. Since the artificial projection is also the only component of the method that can be repeated as often as required, it must be calculated anew for every optimization run to determine the optimum set of imaging parameters.

In some instances DSA sequences are generated by means of so-called biplane x-ray systems. In this instance it is possible to acquire two projection images at two differing angulations, in other words with differing imaging parameters, simultaneously. This facilitates registration compared with a single projection image, since additional information is available from a second viewpoint. In many instances this additional information is sufficient to carry out a unique registration. The orientation of the two two-dimensional projection images is known through the parameters of the biplane x-ray system, so that point correspondences can be determined between the two images of the DSA sequences. However this technique also requires an artificial projection of the three-dimensional volume data record. This procedure is described in detail for example in the dissertation "Räumliche und zeitliche Rekonstruktion in der Neuroradiologie" (Spatial and temporal reconstruction in neuroradiology) by T. Hüllmandel, written in the year 2004 at Julius-Maximilian University in Würzburg.

SUMMARY OF THE INVENTION

The object of the present invention is to create a method for determining a set of imaging parameters, which allows high-quality registration. Registration here should be possible, regardless of whether a biplane x-ray system or a monoplane x-ray system is used, whether or not an individual DSA image is available with a high fill level, etc. It should also not be necessary to determine a summation image based on the DSA sequence.

The object is achieved by the claims.

The present invention relates to a determination method for a set of imaging parameters, with the set of imaging parameters being used to register a three-dimensional volume data record and a two-dimensional projection image in relation to one another. The volume data record here contains a vascular tree. The projection image is an image of an actual fill state, to which the vascular tree is filled with contrast agent at an acquisition time.

According to the invention a computation facility determines a target fill state expected at the acquisition time. The target fill state describes which parts of the vascular tree should be filled with contrast agent in the three-dimensional volume data record at the acquisition time. The computation facility uses the target fill state and the projection image to determine the set of imaging parameters.

The core concept of the present invention is therefore to determine in the three-dimensional volume data set which parts of the vascular tree are (or should be) filled with contrast agent at the acquisition time. Only this part of the vascular tree is used to register the volume data record in relation to the projection image. This procedure is different from the procedure of the prior art, wherein the entire three-dimensional vascular tree is always used to determine the set of imaging parameters.

It is possible to determine the target fill state purely by computation. For example an initial fill state can be defined—purely by computation—and this initial fill state can be extrapolated over time. This type of simulation is known to those skilled in the art as computational fluid dynamics (abbreviated to CFD). By applying the Navier-Stokes equations to a specific vascular system it is possible—with sufficiently accurate calculation and adequate information about the vascular system and other ambient conditions—to simulate the blood flow in a physically correct manner. The complete set of Navier-Stokes equations related to flow simulation is described for example in T. Petrila, D. Trif, "Basics of Fluid Mechanics and Introduction to Computational Fluid Dynamics, Numerical Methods and Algorithms", Springer-Verlag, 2005.

However according to the invention it is preferred that the computation facility determines the target fill state using at least one further two-dimensional projection image and a valid set of imaging parameters for this further projection image and that the further two-dimensional projection image is an image of a further actual fill state, to which the vascular tree is filled with contrast agent at a further acquisition time.

It is possible for the first-mentioned projection image and the further projection image to be acquired with the same imaging parameters. This procedure even represents the norm. Alternatively—in particular when the projection images are acquired using a biplane x-ray system—it is however likewise possible for the first-mentioned projection image and the further projection image to have been acquired with differing imaging parameters.

If the first-mentioned projection image and the further projection image were acquired with differing imaging parameters, the projection images can be acquired either at the same time or at differing times. If however the first-mentioned projection image and the further projection image were acquired with the same imaging parameters, the projection images have to have been acquired at differing times.

If the first-mentioned projection image and the further projection image were acquired at differing times, the computation facility preferably uses the at least one further two-dimensional projection image and the valid set of imaging parameters for this further projection image to determine an initial fill state. The initial fill state here describes which parts of the vascular tree are filled with contrast agent in the three-dimensional volume data record at the further acquisition time. The computation facility then determines the expected target fill state by temporal extrapolation of the initial fill state. In the case of differing acquisition times a two-stage procedure is used, namely determination of an initial fill state first and then temporal extrapolation of the initial fill state.

To implement temporal extrapolation of the initial fill state it is for example possible to deploy the above-mentioned CFD, which is known per se. Alternatively it is for example possible to determine the above-mentioned target fill state based on the initial fill state using a particle-based method. Such procedures are for example described in detail in the earlier German patent application, as yet unpublished by the filing date of the present invention, "Ermittlungsverfahren für einen zeitlichen Verlauf einer örtlich dreidimensional aufgelösten Anwesenheitswahrscheinlichkeitsverteilung einer Substanz in einem Gefäßsystem" (Method for determining a temporal profile of a probability distribution with local three-dimensional resolution for the presence of a substance in a vascular system), filing date Mar. 27, 2007, application number 10 2007 015 306.8. Reference should also be made in this context to the dissertation "Visualisierung von Blutfluss im 3-D aus 2-D Angiogrammen" (Visualization of blood flow in 3D from 2D angiograms) by E.-S. Platzer, Koblenz-Landau University, August 2006.

Until now it has been assumed in the context of the present invention that an individual projection image is to be registered in relation to the volume data record. In a number of cases—even as the norm—there is however a sequence of projection images. The projection images can be native images in the individual instance. Native images here are projection images, from which no other projection image is subtracted. Generally however they are DSA images. Where there is a sequence of projection images, it is possible for the computation facility to execute the last-described determination method (key features: determination of an initial fill state first, then temporal extrapolation of the initial fill state) successively in each instance based on the last-determined set of imaging parameters with a temporally subsequent projection image in the temporal sequence.

In the context of the last-described procedure therefore one of the projection images is selected first. The selected projection image can be for example the temporally first projection image in the sequence. However this is not mandatory. The selected projection image corresponds to the further projection image in the first iteration. One set of imaging parameters—more or less precisely—is estimated for this projection image. The initial fill state is then determined by means of a back projection. The initial fill state is extrapolated temporally in a manner known per se (for example by means of CFD or a particle-based method) and the target fill state is thus determined for the acquisition time, at which the temporally subsequent (generally the immediately temporally subsequent) projection image was acquired. The temporally subsequent projection image and the determined target fill state are then used to determine the new set of imaging parameters.

In the next iteration the projection image, which was used in conjunction with the determined target fill state to determine the set of imaging parameters, is mapped into the volume data record by back projection and a new initial fill state is thus determined. Information about the flow of contrast agent hitherto determined can also be used when determining the new initial fill state. The newly determined initial fill state is again temporally extrapolated and a new target fill state is thus determined. The newly determined target fill state and the again temporally subsequent projection image then represent the input variables, which are used to track the set of imaging parameters yet further. The procedure is repeated until either all the projection images of the sequence have been processed or an abort criterion is reached.

The computation outlay for determining the set of imaging parameters is considerable. This is so regardless of whether the set of imaging parameters is determined in the inventive manner or in a manner known in the prior art. However with the inventive procedure the computation outlay can be reduced in that the computation facility limits a parameter space, within which it determines the set of imaging parameters, further with each new determination of the set of imaging parameters.

The volume data record contains voxels. Each voxel here is either assigned or not assigned to the vascular tree. For each voxel assigned to the vascular tree, the target fill state indicates whether or not the respective voxel is filled with contrast agent at the acquisition time. Furthermore the projection image contains pixels. Each pixel here is either filled or not filled with contrast agent. The computation outlay for examining one set of imaging parameters compared with another set of imaging parameter can be reduced in that the computation facility maps the voxels filled with contrast agent at the acquisition time respectively into the projection image for a number of sets of imaging parameters, respectively determines the number of voxels filled with contrast agent in the volume data record, which are mapped onto pixels filled with contrast agent in the projection image and determines the valid set of imaging parameters in such a manner that the determined number is maximized.

The number of pixels, which are filled with contrast agent in a specific projection image can fluctuate in the context of the sequence from projection image to projection image. To compare the sets of imaging parameters over the projection images, the number of voxels filled with contrast agent, which are mapped onto pixels filled with contrast agent, is therefore inappropriate. However the comparison can be carried out, if the computation facility also determines the number of pixels filled with contrast agent in the respective projection image and determines the ratio of the number of voxels filled with contrast agent in the volume data record, which are mapped onto pixels filled with contrast agent in the projection image on the one hand to the number of pixels filled with contrast agent in the respective projection image on the other hand. The computation facility can use the determined ratio in particular to decide whether further iterations are carried out to determine the optimum set of imaging parameters.

In many instances it will be sufficient to determine the set of imaging parameters using a rigid or affine registration method. In some instances it will however be necessary to use an elastic registration method. Elastic registration methods are known per se. Reference is made purely by way of example to the specialist article "Three-dimensional motion tracking of coronary arteries in biplane cineangiograms" by G. Shechter et al., published in IEEE Transactions on Medical Imaging, vol. 22, number 4, pages 493 to 503, April 2003.

BRIEF DESCRIPTION OF THE DRAWINGS

Further advantages and details will emerge from the description which follows of exemplary embodiments in conjunction with the drawings of basic outlines, in which:
FIG. 6 shows a flow diagram,
FIG. 7 shows a volume data record containing a vascular tree and
FIGS. 8 to 11 show flow diagrams.

DETAILED DESCRIPTION OF THE INVENTION

Figure 1:
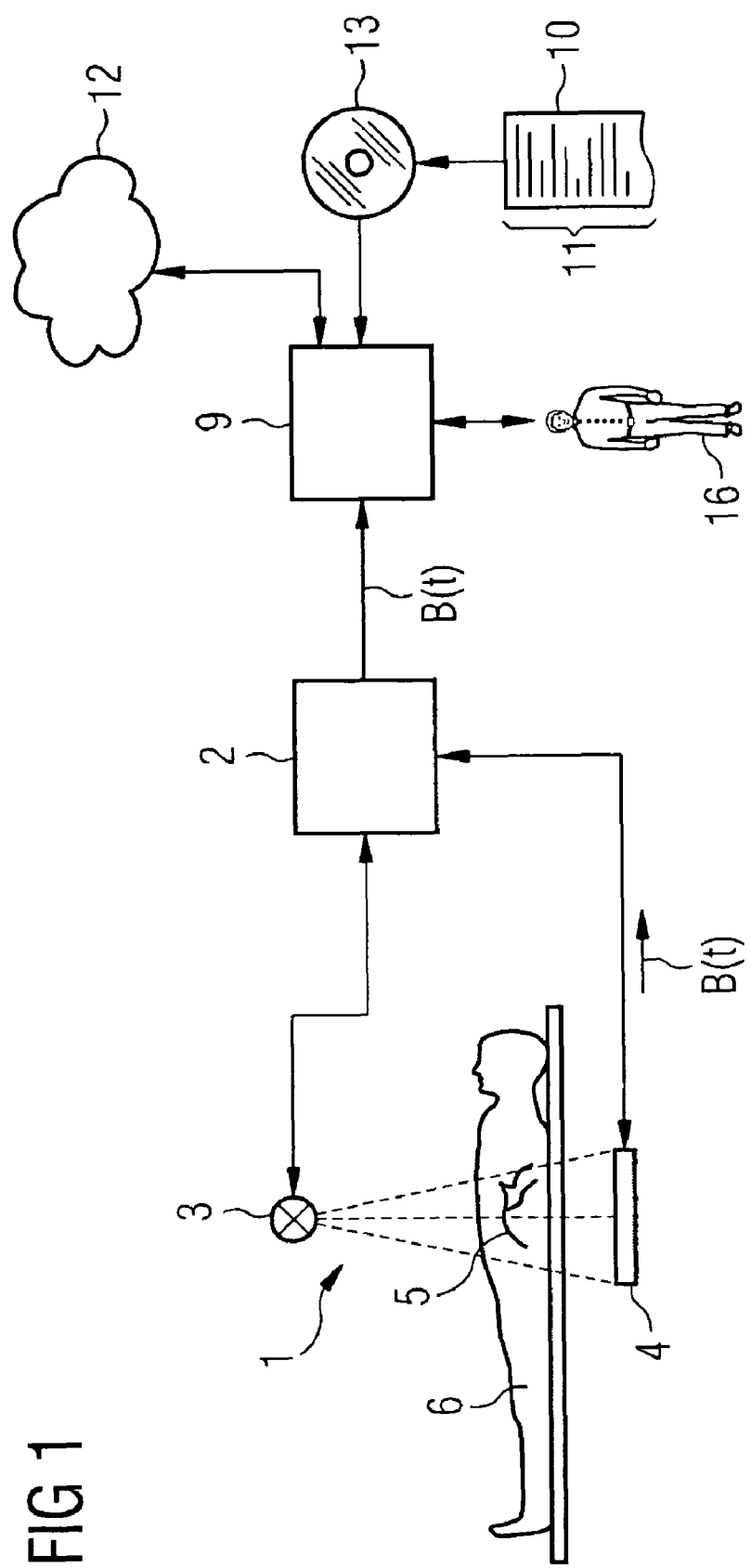
FIG. 1 shows an x-ray system and a computation facility.

According to FIG. 1 an x-ray system has an acquisition facility 1 and a control facility 2. The acquisition facility 1 has an x-ray source 3 and an x-ray detector 4. The acquisition facility 1—after corresponding activation by the control facility 2—acquires a sequence of two-dimensional projection images B. Each of the projection images B is acquired here at a respective acquisition time t. The sequence of projection images B shows the flow of a contrast agent through an actually present (and of course three-dimensional) vascular tree 5. The vascular tree 5 is only shown schematically in FIG. 1. It can be present for example in the brain or in another part of the body of a patient 6. The sequence of projection images B is received by the control facility 2 and buffered there.

FIGS. 2 to 5 shows some of the projection images B in the sequence in a highly schematic manner and purely by way of example.

Figure 2:
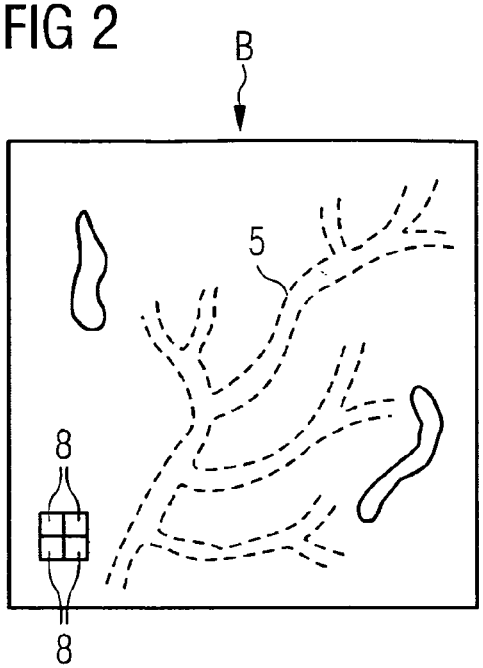
FIGS. 2 to 5 show two-dimensional projection images.

FIG. 2 shows the first projection image B of the sequence. During acquisition of this projection image B there was as yet no contrast agent present in the vascular tree 5. The projection image B in FIG. 2 therefore shows the structure surrounding the vascular tree 5 with relatively poor contrast. The vascular tree 5 is marked with a broken line in FIG. 2. The vascular tree 5 cannot be identified in the respective projection image B if it is not filled with contrast agent. The projection image B according to FIG. 2 can be used for example as a reference image for the other projection images B in the sequence, in order to create a DSA sequence based on the other projection images B in the sequence.

Figure 3:
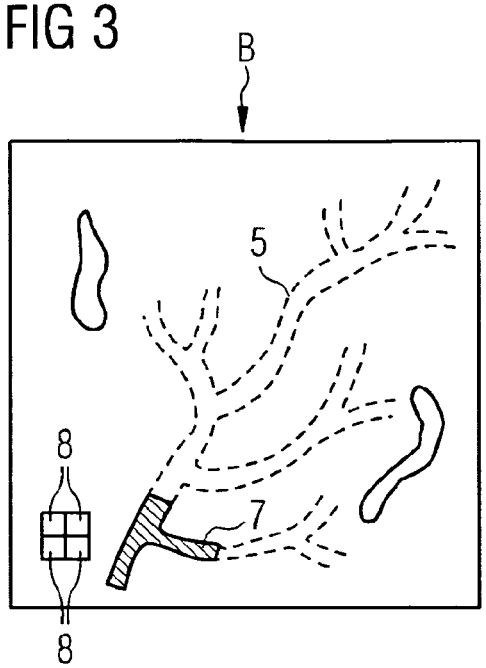

FIG. 3 shows a projection image B in the sequence, in which contrast agent 7 has already flowed into the vascular tree 5. The contrast agent 7 has already been propagated to a degree in the vascular tree 5.

Figure 4:
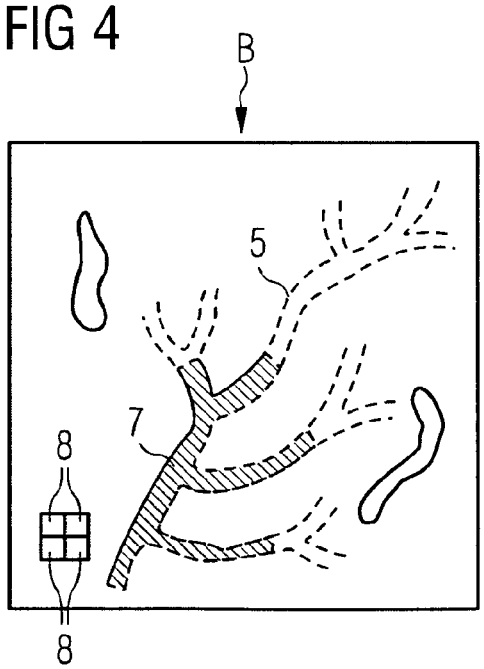

FIG. 4 shows a projection image B in the sequence, in which the contrast agent 7 has already be introduced in its entirety into the vascular tree 5 and been propagated there. To some extent the contrast agent 7 has also already been flushed out of the vascular tree 5, for example having been perfused into the surrounding tissue.

Figure 5:
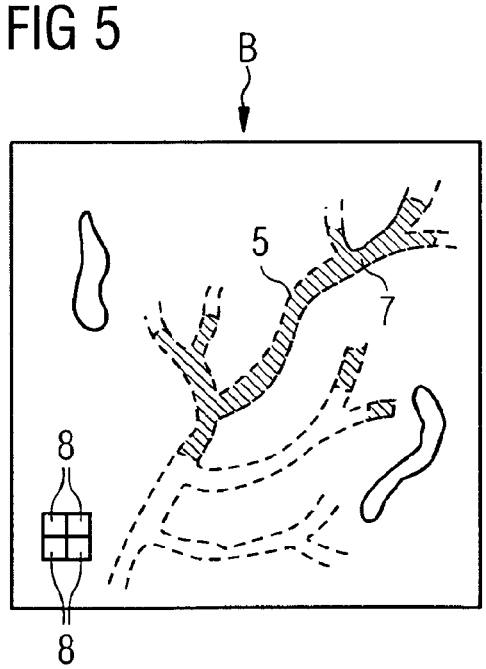

FIG. 5 shows a projection image B from an end stage of the acquisition. At this time the contrast agent 7 has already largely been flushed out of the vascular tree 5 and/or perfused into the tissue surrounding the vascular tree 5.

According to FIGS. 2 to 5 the projection images B have pixels 8. Each pixel 8 has a gray-scale value, which is between a minimum and maximum value, for example between 0 and 255 ($=2^8-1$). It is decided as a function of the gray-scale value whether or not the respective pixel 8 shows the vascular tree 5 filled with contrast agent 7 in the respective projection image B. To simplify matters, the shorter formulation "whether or not the respective pixel 8 is filled with contrast agent 8" is used in relation to the projection images B even if to be precise the respective pixel 8 may not be filled with contrast agent 7 but rather just the part of the vascular tree 5 mapped onto the respective pixel 8.

The sequence of projection images B and the acquisition times t assigned to the projection images B are supplied to a computation facility 9. The computation facility 9 can be identical to the control facility 2. Alternatively it can be configured as a separate facility.

According to FIG. 1 the computation facility 9 is programmed with a computer program 10. During operation of the computation facility 9 the computation facility 9 processes the computer program 10. The processing of the computer program 10 causes the computation facility 9 to execute a determination method, which is described in more detail below.

The computer program 10 comprises machine code 11, which can be processed by the computation facility 9. The processing of the machine code 11 brings about the execution of the above-mentioned determination method.

The computer program 10 can be supplied to the computation facility 9 for example by way of a computer network link 12 (for example a link to the World Wide Web or a local computer network). Alternatively the computer program 10 can be supplied to the computation facility 9 by way of a data medium 13, on which the computer program 10 is stored in machine-readable form. Examples of suitable data media 13 are a CD-ROM (see the illustration in FIG. 1), a USB memory stick, a memory card, etc.

The basic principle of the inventive determination method is described in more detail below in conjunction with FIG. 6.

According to FIG. 6 in a step S1 the computation facility 9 receives the acquired sequence of projection images B and their acquisition times t. The computation facility 9 also generally executes a step S2, in which it uses the acquired sequence of projection images B to determine DSA images. It therefore selects one of the projection images B (generally the temporally first acquired projection image B—see FIG. 2) and subtracts this projection image B in a known manner—for example a linear or logarithmic manner—from the other projection images B. However step S2 is not mandatory. It may be left out in an individual instance. Regardless of whether or not step S2 is present, each of the projection images B is an image of an actual fill state, to which the vascular tree 5 is filled with contrast agent 7 at the corresponding acquisition time.

In a step S3 the computation facility 9 receives a three-dimensional volume data record 14 (see FIG. 7). The volume data record 14 contains the vascular tree 5 (more precisely a three-dimensional reconstruction of the vascular tree 5). The volume data record 14 therefore contains a number of voxels 15. Each voxel 15 here is either assigned to the vascular tree 5 or not assigned to the vascular tree 5.

In the context of the present invention only those voxels 15 assigned to the vascular tree 5 are significant. Only these voxels 15 are therefore considered below.

In a step S4 the computation facility 9 determines a target fill state for (at least) one of the acquisition times t. For each voxel 15 assigned to the vascular tree 5, the target fill state indicates whether or not the respective voxel 15 is filled with contrast agent 7 at this time t. Details of the determination of the target fill state will be examined below. Regardless of the precise nature of the determination however the target fill state describes which parts of the vascular tree 5 should be filled with contrast agent 7 in the three-dimensional volume data record 14 at the relevant acquisition time t. It is also possible for the projection image B, which is to be registered with the volume data record 14 and corresponds to the respective acquisition time t, also to be included in the determination of the target fill state for one of the acquisition times t. Alternatively however it is also possible to determine the target fill state independently of this projection image B.

In a step S5 the computation facility 9 determines a set of imaging parameters P. The set of imaging parameters P describes how the three-dimensional volume data record 14 is mapped into the two-dimensional projection images B. The set of imaging parameters P is therefore used to register the volume data record 14 and the projection images B in relation to one another. The computation facility 9 here determines the set of imaging parameters P in the context of step S5 based on the previously determined target fill state and the corresponding projection image B. The set of imaging parameters P is thus determined based on the relevant projection image B and based on the voxels 15 filled with contrast agent 7 in the vascular tree 5. The voxels 15 not filled with contrast agent 7 in the vascular tree 5 (and of course the other voxels 15 not assigned to the vascular tree 5) are not used to determine the set of imaging parameters P.

In a step S6 the computation facility 9 can then undertake further processing of the volume data record 14 and/or the projection images B. Because the imaging parameters P, which define registration, are now known, it is also possible to carry out combined evaluations in this process.

As mentioned above, it is possible to determine the target fill state purely by computation (in other words without reference to actually acquired blood flow states). In particular determination is possible by means of the above-mentioned CFD. However it is preferable for the computation facility 9 to determine the target fill state using at least one further two-dimensional projection image B and a valid set of imaging parameters P for this further projection image B. The further two-dimensional projection image B here—like the projection image B included in the determination of the set of imaging parameters P in step S5 in FIG. 6—is an image of a (further) actual fill state, to which the vascular tree 5 is filled with contrast agent 7 at a further acquisition time t. To differentiate the individual projection images B, their acquisition times t and the respectively used imaging parameters P, the corresponding variables are assigned an index i below where necessary.

The sequence of projection images B can be acquired, as described above in conjunction with FIG. 1, using the x-ray system shown there. In this instance the projection images B are acquired one after the other, so that an acquisition time $t_i$ specific to the respective projection image $B_i$ can be assigned to each projection image $B_i (i=1, 2, 3, \ldots )$. The acquisition times $t_i$ of the projection images $B_i$ are therefore different from one another. Also the acquisition facility 1 is generally held in a constant position during acquisition of the sequence of projection images $B_i$. The (actual) imaging parameters of the projection images $B_i$ are therefore identical to one another—provided that the vascular tree 5 per se does not move and is also not moved. All the projection images $B_i$ are therefore acquired with the same (actual) imaging parameters. In this instance it is advantageous to modify the procedure in FIG. 6, which is described in more detail below in conjunction with FIG. 8. FIG. 8 shows only the embodiment of steps S4 and S5 in FIG. 6. Steps S1 to S3 and S6 can remain unchanged.

According to FIG. 8 in a step S11 the computation facility 9 first sets the index i to an initial value, for example the value zero. In a step S12 it also determines a preliminary set of imaging parameters $P_i$. Step S12 can hereby be implemented with the involvement of a user 16 (see FIG. 1). Alternatively fully automatic implementation is possible. For example the actual recording geometry may be known precisely and the position of the patient 6 may be roughly known, so that an—initially relatively imprecise—approximate determination of the imaging parameters $P_i$ can be undertaken.

In a step S13 the computation facility 9 selects the projection image $B_i$ defined by the index i.

In a step S14 the computation facility 9 uses the projection image $B_i$ selected in step S13 and the currently valid set of imaging parameters $P_i$ to determine an initial fill state. The initial fill state corresponds by its nature to the target fill state. It describes which parts of the vascular tree 5 are filled with contrast agent 7 in the three-dimensional volume data record 14 at acquisition time to of the currently selected projection image $B_i$. The determination in step S14 in particular includes a back projection of the projection image $B_i$ into the volume data record 14 using the currently valid set of imaging parameters $P_i$. In the context of step S14 the computation facility 9 determines which parts of the vascular tree 5 would be mapped onto the pixels 8 filled with contrast agent 7 in the selected projection image $B_i$ and marks these voxels 15 as filled with contrast agent 7. If information about the fill state of the vascular tree 5 is already known from previous iterations (see below), this information can also be taken into account in the context of step S14.

Step S14 is known per se. Reference is made purely by way of example to DE 10 2004 018 499 A1, DE 100 00 185 A1, DE 101 00 572 A1 and the earlier German patent application 10 2007 015 306.8 by the applicant as yet unpublished at the filing date of the present application.

In a step S15 the computation facility 9 increments the index i. It therefore increases its value by an increment, for example by one.

In a step S16 the computation facility 9 determines the target fill state expected at the acquisition time $t_i$ now selected by temporal extrapolation of the initial fill state determined in step S14. The determination of the target fill state takes into account the local blood flow direction and the local or general blood flow speed as well as the initial fill state. Experiments have shown that the procedure described in the German patent application 10 2007 015 306.8 in particular produces particularly good results. Other procedures can however also be used.

In a step S17 the computation facility 9 uses the target fill state determined in step S16 and the projection image $B_i$ defined by the current value of the index i to determine a new set of imaging parameters $P_i$. The incrementation of the index i in step S15 means that a different projection image $B_i$ is used in step S17 from the one in step S14. Step S17 in FIG. 8 corresponds essentially to step S5 in FIG. 6.

In a step S18 the computation facility 9 checks whether the determination of the imaging parameters $P_i$ should be terminated. If not, the computation facility 9 returns to step S14.

In principle it is possible to leave out step S18, so that steps S14 to S17 are only processed once. Iterative processing, whereby the computation facility 9, executes the determination method successively in each instance based on the last-determined set of imaging parameters $P_i$, with a subsequent, for example the respective next, projection image $P_i$ in the temporal sequence of projection images $B_i$, is however preferred. This is because it is possible in particular to improve the accuracy, with which the determined imaging parameters $P_i$ correspond to the optimum imaging parameters, with every iteration.

As already mentioned above, determination of the imaging parameters $P_i$ requires a considerable computation outlay. The computation outlay increases with the size of a parameter space, within which the computation facility 9 determines the set of imaging parameters $P_i$. In a particularly preferred embodiment of the present invention it is therefore possible to insert a step S19 in the no-branch of step S18, in which the computation facility 9 limits the parameter space further in each instance. This allows the computation outlay to be reduced from iteration to iteration.

To determine the imaging parameters P it is necessary to find a measure for already defined imaging parameters P of how good said imaging parameters P actually are. Step S5 in FIG. 6 and step S17 in FIG. 8 can be implemented in a different manner for this purpose. They can in particular be implemented in a manner known per se in the prior art. However a procedure described in more detail below in conjunction with FIG. 9 is preferred. According to FIG. 9 step S5 and step S17 are subdivided into three steps S21, S22 and S23.

In step S21 the computation facility 9 determines a number of sets of imaging parameters P—generally based on the currently valid set of imaging parameters $P_i$. For example the computation facility 9 can cover the parameter space uniformly or vary each parameter P individually.

In step S22 the computation facility 9 selects one of the sets of imaging parameters P from step S21 in each instance. In the context of step S22 the computation facility 9 uses the respectively selected set of imaging parameters P to map the voxels 15 filled with contrast agent 7 at time $t_i$ into the corresponding projection image $B_i$. In the context of step S22 it also respectively determines the number of voxels filled with contrast agent 7 in the volume data record 14, which are mapped onto pixels 8 filled with contrast agent 7 in the corresponding projection image $B_i$.

In the context of step S23 the computation facility 9 finally determines the valid set of imaging parameters $P_i$. The set of imaging parameters $P_i$ determined in the context of step S23 is either final or is rated as valid in the context of the next iteration. The computation facility 9 hereby determines the valid set of imaging parameters $P_i$ in such a manner that it maximizes the number of voxels 15 filled with contrast agent 7 in the volume data record 14, which are mapped onto the pixels 8 filled with contrast agent 7 in the corresponding projection image $B_i$. For example the computation facility 9 can adopt the set of imaging parameters P, in which the number of voxels 15 determined in the context of step S22 is at a maximum. It can also define partial derivations of the number according to one of the imaging parameters P in each instance in the parameter space and then carry out a step in the direction of the gradient (=maximum increase).

The number of voxels 15 filled with contrast agent 7 in the volume data record 14, which are mapped onto pixels 8 filled with contrast agent 7 in the projection image $B_i$, represents a quality measure for the correspondence of the respective set of imaging parameters $P_i$. The quality measures are hereby directly comparable within the same projection image $B_i$. However the quality measure is not comparable over projection images. Therefore steps S21 to S23 are preferably replaced by steps S31 to S34 according to FIG. 10 and steps S18 and S19 in FIG. 8 are modified to steps S35 to S37.

In step S31 the computation facility 9 determines the number of pixels 8 filled with contrast agent 7 in the currently selected projection image $B_i$.

Step S32 corresponds to step S21 in FIG. 9. Step S33 corresponds essentially to step S22 in FIG. 9. However the computation facility 9 also divides the numbers of voxels 15 determined in the context of step S33 by the number of pixels 8 determined in step S31. The ratios thus obtained can be compared across projection images. Step S34 corresponds to step S23 in FIG. 9 in its approach.

The quality measure determined by the quotient formation—and in particular the temporal profile of the quality measure—can be used in particular to determine whether further iterations, in other words further processing of steps S14 to S17 in FIG. 8 should be undertaken to determine the optimum set of imaging parameters P. For example step S18 in FIG. 8 can be subdivided into steps S35 and S36 for this purpose.

In step S35 the computation facility 9 determines the value of a logical variable OK, which it interrogates in step S36. The logical variable OK here is a function on the one hand of the quality measure or the temporal profile of the quality measure and on the other hand a function of the index i. In particular the logical variable OK can assume the value TRUE, when the index i reaches (or exceeds) its maximum value or the quality measure or temporal profile of the quality measure satisfies an abort condition. If however the abort condition is not satisfied and the index i does not reach (or exceed) its maximum value, the logical variable OK assumes the value UNTRUE.

FIG. 10 shows an embodiment of step S19 in FIG. 8 in step S37. Step S37 here corresponds essentially to step S19 in FIG. 8. The imaging parameters $P_i$ are limited in the context of step S37 but as a function of the quality measure achieved or the temporal profile of the quality measure.

The imaging parameters P and $P_i$ can be determined in the context of steps S5 in FIG. 6, S17 in FIG. 8, S21 to S23 in FIG. 9 and S31 to S34 in FIG. 10 using a rigid registration method or using an affine registration method. In many instances this procedure produces a completely satisfactory result. If a particularly high-quality registration is required or the vascular tree 5 is subject in reality to deformation and motion, it can however be expedient—as shown by way of example in step S5 in FIG. 6—to determine the set of imaging parameters P using an elastic registration method. Elastic registration methods are known per se. Reference is made to the specialist article by G. Shechter mentioned above.

Up to now in the instance described the x-ray system used to acquire the projection images B is configured as a monoplane x-ray system, whose acquisition facility 1 was not moved during acquisition of the projection images B. As mentioned above this embodiment represents the norm but it is not mandatory. It is possible instead to use a biplane x-ray system—which is known per se—and to acquire two differing projection images B simultaneously using differing imaging parameters. It is also possible as an alternative to acquire two projection images B in temporal succession from differing angulations. This last-mentioned procedure can be carried out either using a monoplane x-ray system or a biplane x-ray system. The processing of two respectively two-dimensional projection images B acquired from differing angulations is described in more detail below with reference to FIG. 11.

According to FIG. 11 the computation facility 9 receives the projection images in a step S41. To differentiate the two projection images and the corresponding acquisition times from one another, the two projection images in the context of the descriptions relating to FIG. 11 are shown with reference characters B and B' while the corresponding acquisition times are shown with the reference characters t and t'.

The computation facility 9 can receive the acquisition times t, t' likewise in the context of step S41. However this is only necessary, if the two acquisition times t, t' differ from one another. As an alternative to the acquisition times t, t' the computation facility 9 could also receive the difference between the acquisition times t, t'. Step S41 in FIG. 11 corresponds to step S1 in FIG. 6 in its approach.

In a step S42 the computation facility 9 receives the volume data record 14. Step S42 in FIG. 11 corresponds to step S3 in FIG. 6.

In a step S43 the computation facility 9 selects one of the projection images B, B'—for example the projection image B'—, defines a set of imaging parameters P' for this projection image B' and uses the selected projection image B' and the valid set of imaging parameters P' for this projection image B' to determine an initial fill state. Step S43 in FIG. 11 corresponds essentially to steps S13 and S14 in FIG. 8.

In a step S44 the computation facility 9 checks whether the two projection images B, B' have identical or differing acquisition times t, t'. If the acquisition times t, t' are identical, in a step S45 the computation facility 9 adopts the initial fill state determined in step S43 as the target fill state. If the acquisition times t, t' differ, in a step S46 the computation facility 9 determines the target fill state by temporal extrapolation of the initial fill state. Step S46 in FIG. 11 corresponds essentially to step S16 in FIG. 8.

In a step S47 the computation facility 9 uses the target fill state and the other of the projection images B, B'—for example the projection image B—to determine a set of imaging parameters P for the other projection image B. Step S47 in FIG. 11 corresponds essentially to steps S5 and S17 in FIGS. 6 and 8.

The present invention has many advantages. Some of these advantages are listed below.

The present invention allows a dynamic registration between the two-dimensional projection images B and the three-dimensional volume data record 14, without it being necessary first to extract information about blood flow from the sequence of two-dimensional projection images B and then add this.

Use of a biplane angiography system is possible but not mandatory. There is no need for an artificial projection of the entire vascular tree 5.

The quality measure described in conjunction with FIGS. 9 and 10 allows the optimum set of imaging parameters P to be determined in an effective and efficient manner.

Since the projection images B are used to determine the respective target fill state in particular in conjunction with the iterating procedure described in FIG. 8, it is ensured that the determined target fill states correspond to the fill states actually present apart from minor deviations. Particularly good results are obtained here, if the target fill states are determined using particle-based determination methods.

Registration accuracy increases with the amount of information obtained by way of the progressive blood flow. The parameter search space can also be clearly limited with increasing accuracy. In some instances determination of the optimum set of imaging parameters P can even be aborted prematurely (in other words before the index i reaches its maximum value).

The quality measure described in conjunction with FIGS. 9 and 10 means that a—generally very complex—feature extraction in an artificial projection of the volume data record 14 and in the real projection images B can be dispensed with.

The inventive procedure allows not only registration for a vascular system filled in its entirety with contrast agent but also registration with an individual projection image B or a few projection images B in the acquired sequence.

The use of only one individual projection image B respectively for each temporal and registration step means that there are fewer motion artifacts than with the prior art. It is therefore easier to compensate for motion. Further errors present due to motion can also be compensated for in particular in conjunction with the use of elastic registration methods.

The method can be fully automated. It can in particular be integrated into the method for blood flow reconstruction described in the above-mentioned German patent application 10 2007 015 306.8.

Registration is possible at any acquisition time t for the blood flow that has already taken place. This increases registration flexibility and can save or at least reduce unnecessary computation outlay.

The above description serves solely to describe the present invention. The scope of protection of the present invention should however only be defined by the accompanying claims.

The invention claimed is:

1. A method for determining an imaging parameter for registering a three-dimensional volume data record of an object comprising a vascular tree with a two-dimensional projection image of the object comprising the vascular tree being filled with a contrast agent at an acquisition time, comprising:
   determining a target fill state time describing which parts of the vascular tree are filled with the contrast agent in the three-dimensional volume data record at the acquisition time; and
   determining the imaging parameter based on the target fill state and the two-dimensional projection image for registering the volume data record with the projection image,
   wherein:
      the volume data record comprises voxels being assigned to the vascular tree,
      the target fill state indicates whether the voxels are filled with the contrast agent at the acquisition time,
      the projection image comprises pixels being filled with the contrast agent,
      the voxels filled with the contrast agent at the acquisition time are mapped into the projection image,
      a number of the voxels that are filled with the contrast agent in the volume data record and mapped into the projection image is determined, and
      the imaging parameter is determined to maximize the number of the voxels.

2. The method as claimed in claim 1, wherein a further two-dimensional projection image comprising the vascular tree being filled with the contrast agent is recorded at a further acquisition time.

3. The method as claimed in claim 2, wherein the target fill state is determined based on the further two-dimensional projection image and a further imaging parameter for the further projection image.

4. The method as claimed in claim 2, wherein the projection image and the further projection image are recoded with an identical recording imaging parameter.

5. The method as claimed in claim 2, wherein projection image and the further projection image are recorded with different recording imaging parameters.

6. The method as claimed in claim 2, wherein the acquisition time and the further acquisition time are identical.

7. The method as claimed in claim 2, wherein the acquisition time and the further acquisition time are different.

8. The method as claimed in claim 7, wherein:
   an initial fill state is determined based on the further projection image and the further imaging parameter for the further projection image,
   the initial fill state describes which parts of the vascular tree are filled with the contrast agent in the three-dimensional volume data record at the further acquisition time, and
   the target fill state is determined by a temporal extrapolation of the initial fill state.

9. The method as claimed in claim 8, wherein the imaging parameter is iteratively determined based on a last-determined imaging parameter and a temporally subsequent recorded projection image.

10. The method as claimed in claim 9, wherein the imaging parameter is limited in a parameter space.

11. The method as claimed in claim 1, wherein:
   a number of the pixels being filled with the contrast agent in the projection image is determined, and
   a ratio of the number of the voxels filled with the contrast agent in the volume data record and mapped into the projection image to the number of the pixels filled with the contrast agent in the projection image is calculated, and
   whether a further iteration is carried out is determined based on the ratio so that an optimum imaging parameter is determined.

12. The method as claimed in claim 1, wherein the imaging parameter is determined using an elastic registration method.

13. The method as claimed in claim 1, wherein the projection image is a digital subtraction angiography image.

14. A memory device for storing a computer program in a machine readable form for determining an imaging parameter for registering a three-dimensional volume data record of an object comprising a vascular tree with a two-dimensional projection image of the object comprising the vascular tree being filled with a contrast agent at an acquisition time, comprising:
   a computer program that:
      determines a target fill state time describing which parts of the vascular tree are filled with the contrast agent in the three-dimensional volume data record at the acquisition time; and
      determines the imaging parameter based on the target fill state and the two-dimensional projection image for registering the volume data record with the projection image,
   wherein:
      the volume data record comprises voxels being assigned to the vascular tree,
      the target fill state indicates whether the voxels are filled with the contrast agent at the acquisition time,
      the projection image comprises pixels being filled with the contrast agent,
      the voxels filled with the contrast agent at the acquisition time are mapped into the projection image,
      a number of the voxels that are filled with the contrast agent in the volume data record and mapped into the projection image is determined, and
      the imaging parameter is determined to maximize the number of the voxels.

15. A computer for determining an imaging parameter for registering a three-dimensional volume data record of an object comprising a vascular tree with a two-dimensional projection image of the object comprising the vascular tree being filled with a contrast agent at an acquisition time, comprising:
   a processing unit that:

determines a target fill state time describing which parts of the vascular tree are filled with the contrast agent in the three-dimensional volume data record at the acquisition time; and determines the imaging parameter based on the target fill state and the two-dimensional projection image for registering the volume data record with the projection image, wherein:

the volume data record comprises voxels being assigned to the vascular tree, the target fill state indicates whether the voxels are filled with the contrast agent at the acquisition time, the projection image comprises pixels being filled with the contrast agent, the voxels filled with the contrast agent at the acquisition time are mapped into the projection image, a number of the voxels that are filled with the contrast agent in the volume data record and mapped into the projection image is determined, and the imaging parameter is determined to maximize the number of the voxels.

* * * * *